(12) United States Patent
Jiang

(10) Patent No.: US 11,970,698 B2
(45) Date of Patent: Apr. 30, 2024

(54) LIPOTEICHOIC ACID (LTA) APTAMERS AND ASSOCIATED METHODS

(71) Applicant: Fresenius Medical Care Holdings, Inc., Waltham, MA (US)

(72) Inventor: Tao Jiang, Knoxville, TN (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 17/591,508

(22) Filed: Feb. 2, 2022

(65) Prior Publication Data

US 2022/0243207 A1 Aug. 4, 2022

Related U.S. Application Data

(60) Provisional application No. 63/145,632, filed on Feb. 4, 2021.

(51) Int. Cl.
*C12N 15/115* (2010.01)

(52) U.S. Cl.
CPC ........ *C12N 15/115* (2013.01); *C12N 2310/16* (2013.01)

(58) Field of Classification Search
CPC .............. C12N 15/115; C12N 2310/16; C12N 2310/531
See application file for complete search history.

(56) References Cited

U.S. PATENT DOCUMENTS

| | | | |
|---|---|---|---|
| 2009/0186342 A1 | 7/2009 | Bruno et al. | |
| 2014/0011200 A1 | 1/2014 | Bruno et al. | |
| 2020/0249228 A1 | 8/2020 | Jiang et al. | |

FOREIGN PATENT DOCUMENTS

| | | |
|---|---|---|
| WO | 2012/081908 A2 | 6/2012 |
| WO | 2020/160040 A1 | 6/2020 |

OTHER PUBLICATIONS

Chen "Development of violet membrane biophotonic chip for detection of adenosine triphosphate, gram-positive bacteria and leukocytes" Retrieved from the Internet: URL:https://hdl.handle.net/11296/44hc88 [retrieved on Apr. 6, 2022].
Dua et al. "Cell-SELEX Based Identification of an RNA Aptamer for *Escherichia coli* and Its Use in Various Detection Formats" Mol. Cells, vol. 39, No. 11 (Nov. 2016) pp. 807-813.
Han et al. "In vitro selection of RNA aptamer specific to *Staphylococcus aureus*" Annals of Microbiology, vol. 101. 64 , No. 2 , Oct. 5, 2013, pp. 883-885.
Hong et al. "Single-Stranded DNA Aptamers against Pathogens and Toxins: Identification and Biosensing Applications" Biomed Research International vol. 2015 (Jun. 2015) pp. 1-31.
International Search Report for International Application No. PCT/US2022/014975, dated Jul. 11, 2022, 10 pages.
International Written Opinion for International Application No. PCT/US2022/014975, dated Jul. 11, 2022, 12 pages.
Ellington et al. "In vitro selection of RNA molecules that bind specific ligands" Nature (Aug. 1990) 346(6287) pp. 818-822.
Gold et al. "Aptamers and the RNA world, past and present." Cold Spring Harb. Perspect. Biol. (Mar. 2012) 4(3), a003582.
Schütze et al. "Probing the SELEX Process with Next-Generation Sequencing" PLoS ONE 6(12): e29604 (Dec. 2011). DOI: 10.1371/journal.pone.0029604.
Tadler et al. "Sandwich immunoassay for the detection of lipoteichoic acid" Journal of Clinical Laboratory Analysis. 3(1): 21-25 (1989) Last accessed Feb. 3, 2022 https://www.deepdyve.com/lp/wiley/sandwich-immunoassay-for-the-detection-of-lipoteichoic-acid-OZGZCVZIGj?utm_source=shareEmail&utm_medium=email&utm_campaign=docViewShareButton.
Tuerk et al. "Systematic evolution of ligands by exponential enrichment: RNA ligands to bacteriophage t4 DNA polymerase." Science (Aug. 1990) vol. 249, Issue 4968, pp. 505-510.
Wang et al. "Particle Display: A Quantitative Screening Method for Generating High-Affinity Aptamers" Angewandte Communications International Edition 53(19): pp. 4796-4801 (May 2014). DOI: 10.1002/anie.201309334.
Zhuo et al. "Recent Advances in SELEX Technology and Aptamer Applications in Biomedicine" Int. J. Mol. Sci. (Oct. 2017) 18(10), 2142; doi:10.3390/ijms18102142.
Zuker "Mfold web server for nucleic acid folding and hybridization prediction." Nucleic Acids Res. vol. 31, Issue 13, pp. 3406-3415 (Jul. 2003).

*Primary Examiner* — J. E. Angell
(74) *Attorney, Agent, or Firm* — TraskBritt

(57) ABSTRACT

Described are a number of aptamers that are specific to bind with lipoteichoic acid (LTA), and associated methods.

20 Claims, 10 Drawing Sheets

Specification includes a Sequence Listing.

SEQ ID NO:1

CGA GGC TCT CGG GAC GAC CTG TCG TCA GGA AAA ACG AAA ACC CTA AGG GTC GTC CCG CCT TTA GGA TTT ACA G

Sequence (5' ≥ 3')

SEQ ID NO:2

CGA GGC TCT CGG GAC GAC CAG TCG GCC CGA AAA CAA TAT AAA TCC GAG GTC GTC CCG CCT TTA GGA TTT ACA G

Sequence (5' ≥ 3')

SEQ ID NO:3

CGA GGC TCT CGG GAC GAC GTA GTC GTC ACA CAA GCT GGT TAT CCA AAA
GTC GTC CCG CCT TTA GGA TTT ACA G

Sequence (5' ≥ 3')

SEQ ID NO:4

CGA GGC TCT CGG GAC GAC GAA GTC GCC ACG TAA ACC GAC GAC CGT CAG GTC GTC CCG CCT TTA GGA TTT ACA G

Sequence (5' ≥ 3')

SEQ ID NO:5

CGA GGC TCT CGG GAC GAC GTG GCG GCC CGA AAA CAG ATA AAT CAT AAA GTC GTC CCG CCT TTA GGA TTT ACA G

Sequence (5' ≥ 3')

SEQ ID NO:6

CGA GGC TCT CGG GAC GAC AAA GGA GTC ACG AAA ACA ATA AAG ACT AAA GTC GTC CCG CCT TTA GGA TTT ACA G

Sequence (5' ≥ 3')

SEQ ID NO:7

CGA GGC TCT CGG GAC GAC AAA GGA GTC ACG AAA ACA ATA AAG ACT AAA GTC GTC CCG CCT TTA GGA TTT ACA G

Sequence (5' ≥ 3')

SEQ ID NO:8

CGA GGC TCT CGG GAC GAC GAG ACA CGC TAG TAT CGA AGC GGC CCA AAA
GTC GTC CCG CCT TTA GGA TTT ACA G

Sequence (5' ≥ 3')

SEQ ID NO:9

CGA GGC TCT CGG GAC GAC TTG TCG GAC CGA CTG GTG ATA AAC CCT ATG GTC GTC CCG CCT TTA GGA TTT ACA G

Sequence (5' ≥ 3')

SEQ ID NO:10

CGA GGC TCT CGG GAC GAC AAT AAC CGA AGG GCA TTG CCG CCT CCA AAA
GTC GTC CCG CCT TTA GGA TTT ACA G

Sequence (5' ≥ 3')

SEQUENCE LISTING

```
<160> NUMBER OF SEQ ID NOS: 24

<210> SEQ ID NO 1
<211> LENGTH: 73
<212> TYPE: DNA
<213> ORGANISM: Artificial Sequence
<220> FEATURE:
<223> OTHER INFORMATION: LTA Aptamer 1

<400> SEQUENCE: 1
```

```
cgaggctctc gggacgacct gtcgtcagga aaaacgaaaa ccctaagggt cgtcccgcct    60
ttaggattta cag                                                      73

<210> SEQ ID NO 2
<211> LENGTH: 73
<212> TYPE: DNA
<213> ORGANISM: Artificial Sequence
<220> FEATURE:
<223> OTHER INFORMATION: LTA Aptamer 2

<400> SEQUENCE: 2
cgaggctctc gggacgacca gtcggcccga aaacaatata aatccgaggt cgtcccgcct    60
ttaggattta cag                                                      73

<210> SEQ ID NO 3
<211> LENGTH: 73
<212> TYPE: DNA
<213> ORGANISM: Artificial Sequence
<220> FEATURE:
<223> OTHER INFORMATION: LTA Aptamer 3

<400> SEQUENCE: 3
cgaggctctc gggacgacgt agtcgtcaca caagctggtt atccaaaagt cgtcccgcct    60
ttaggattta cag                                                      73

<210> SEQ ID NO 4
<211> LENGTH: 73
<212> TYPE: DNA
<213> ORGANISM: Artificial Sequence
<220> FEATURE:
<223> OTHER INFORMATION: LTA Aptamer 4

<400> SEQUENCE: 4
cgaggctctc gggacgacga agtcgccacg taaaccgacg accgtcaggt cgtcccgcct    60
ttaggattta cag                                                      73

<210> SEQ ID NO 5
<211> LENGTH: 73
<212> TYPE: DNA
<213> ORGANISM: Artificial Sequence
<220> FEATURE:
<223> OTHER INFORMATION: LTA Aptamer 5

<400> SEQUENCE: 5
cgaggctctc gggacgacgt ggcggcccga aaacagataa atcataaagt cgtcccgcct    60
ttaggattta cag                                                      73

<210> SEQ ID NO 6
<211> LENGTH: 73
<212> TYPE: DNA
<213> ORGANISM: Artificial Sequence
<220> FEATURE:
<223> OTHER INFORMATION: LTA Aptamer 6

<400> SEQUENCE: 6
cgaggctctc gggacgacaa aggagtcacg aaaacaataa agactaaagt cgtcccgcct    60
ttaggattta cag                                                      73

<210> SEQ ID NO 7
<211> LENGTH: 73
<212> TYPE: DNA
```

```
<213> ORGANISM: Artificial Sequence
<220> FEATURE:
<223> OTHER INFORMATION: LTA Aptamer 7

<400> SEQUENCE: 7
cgaggctctc gggacgacgt cgtcgaccca agaacaataa agcttaaagt cgtcccgcct    60
ttaggattta cag                                                      73

<210> SEQ ID NO 8
<211> LENGTH: 73
<212> TYPE: DNA
<213> ORGANISM: Artificial Sequence
<220> FEATURE:
<223> OTHER INFORMATION: LTA Aptamer 8

<400> SEQUENCE: 8
cgaggctctc gggacgacga gacacgctag tatcgaagcg gcccaaaagt cgtcccgcct    60
ttaggattta cag                                                      73

<210> SEQ ID NO 9
<211> LENGTH: 73
<212> TYPE: DNA
<213> ORGANISM: Artificial Sequence
<220> FEATURE:
<223> OTHER INFORMATION: LTA Aptamer 9

<400> SEQUENCE: 9
cgaggctctc gggacgactt gtcggaccga ctggtgataa accctatggt cgtcccgcct    60
ttaggattta cag                                                      73

<210> SEQ ID NO 10
<211> LENGTH: 73
<212> TYPE: DNA
<213> ORGANISM: Artificial Sequence
<220> FEATURE:
<223> OTHER INFORMATION: LTA Aptamer 10

<400> SEQUENCE: 10
cgaggctctc gggacgacaa tacccgaagg gcattgccgc ctccaaaagt cgtcccgcct    60
ttaggattta cag                                                      73

<210> SEQ ID NO 11
<211> LENGTH: 30
<212> TYPE: DNA
<213> ORGANISM: Artificial Sequence
<220> FEATURE:
<223> OTHER INFORMATION: Core Sequence 1

<400> SEQUENCE: 11
ctgtcgtcag gaaaaacgaa aaccctaagg                                    30

<210> SEQ ID NO 12
<211> LENGTH: 30
<212> TYPE: DNA
<213> ORGANISM: Artificial Sequence
<220> FEATURE:
<223> OTHER INFORMATION: Core Sequence 2

<400> SEQUENCE: 12
cagtcggccc gaaaacaata taaatccgag                                    30

<210> SEQ ID NO 13
<211> LENGTH: 30
```

```
<212> TYPE: DNA
<213> ORGANISM: Artificial Sequence
<220> FEATURE:
<223> OTHER INFORMATION: Core Sequence 3

<400> SEQUENCE: 13
gtagtcgtca cacaagctgg ttatccaaaa                               30

<210> SEQ ID NO 14
<211> LENGTH: 30
<212> TYPE: DNA
<213> ORGANISM: Artificial Sequence
<220> FEATURE:
<223> OTHER INFORMATION: Core Sequence 4

<400> SEQUENCE: 14
gaagtcgcca cgtaaaccga cgaccgtcag                               30

<210> SEQ ID NO 15
<211> LENGTH: 30
<212> TYPE: DNA
<213> ORGANISM: Artificial Sequence
<220> FEATURE:
<223> OTHER INFORMATION: Core Sequence 5

<400> SEQUENCE: 15
gtggcggccc gaaaacagat aaatcataaa                               30

<210> SEQ ID NO 16
<211> LENGTH: 30
<212> TYPE: DNA
<213> ORGANISM: Artificial Sequence
<220> FEATURE:
<223> OTHER INFORMATION: Core Sequence 6

<400> SEQUENCE: 16
aaaggagtca cgaaaacaat aaagactaaa                               30

<210> SEQ ID NO 17
<211> LENGTH: 30
<212> TYPE: DNA
<213> ORGANISM: Artificial Sequence
<220> FEATURE:
<223> OTHER INFORMATION: Core Sequence 7

<400> SEQUENCE: 17
gtcgtcgacc caagaacaat aaagcttaaa                               30

<210> SEQ ID NO 18
<211> LENGTH: 30
<212> TYPE: DNA
<213> ORGANISM: Artificial Sequence
<220> FEATURE:
<223> OTHER INFORMATION: Core Sequence 8

<400> SEQUENCE: 18
gagacacgct agtatcgaag cggcccaaaa                               30

<210> SEQ ID NO 19
<211> LENGTH: 30
<212> TYPE: DNA
<213> ORGANISM: Artificial Sequence
<220> FEATURE:
<223> OTHER INFORMATION: Core Sequence 9

<400> SEQUENCE: 19
```
ttgtcggacc gactggtgat aaaccctatg        30

<210> SEQ ID NO 20
<211> LENGTH: 30
<212> TYPE: DNA
<213> ORGANISM: Artificial Sequence
<220> FEATURE:
<223> OTHER INFORMATION: Core Sequence 10

<400> SEQUENCE: 20
aatacccgaa gggcattgcc gcctccaaaa        30

<210> SEQ ID NO 21
<211> LENGTH: 30
<212> TYPE: DNA
<213> ORGANISM: Artificial Sequence
<220> FEATURE:
<223> OTHER INFORMATION: DNA aptamer core sequence
<220> FEATURE:
<221> NAME/KEY: R
<222> LOCATION: (1)..(1)
<223> OTHER INFORMATION: A or G
<220> FEATURE:
<221> NAME/KEY: W
<222> LOCATION: (2)..(2)
<223> OTHER INFORMATION: A or T
<220> FEATURE:
<221> NAME/KEY: V
<222> LOCATION: (3)..(3)
<223> OTHER INFORMATION: A, C, or G
<220> FEATURE:
<221> NAME/KEY: B
<222> LOCATION: (5)..(5)
<223> OTHER INFORMATION: C, G, or T
<220> FEATURE:
<221> NAME/KEY: V
<222> LOCATION: (6)..(6)
<223> OTHER INFORMATION: A, C, or G
<220> FEATURE:
<221> NAME/KEY: H
<222> LOCATION: (8)..(8)
<223> OTHER INFORMATION: A, C, or T
<220> FEATURE:
<221> NAME/KEY: M
<222> LOCATION: (10)..(10)
<223> OTHER INFORMATION: A or C
<220> FEATURE:
<221> NAME/KEY: S
<222> LOCATION: (11)..(11)
<223> OTHER INFORMATION: C or G
<220> FEATURE:
<221> NAME/KEY: R
<222> LOCATION: (12)..(12)
<223> OTHER INFORMATION: A or G
<220> FEATURE:
<221> NAME/KEY: R
<222> LOCATION: (14)..(14)
<223> OTHER INFORMATION: A or G
<220> FEATURE:
<221> NAME/KEY: M
<222> LOCATION: (16)..(17)
<223> OTHER INFORMATION: A or C
<220> FEATURE:
<221> NAME/KEY: R
<222> LOCATION: (18)..(18)
<223> OTHER INFORMATION: A or G
<220> FEATURE:
<221> NAME/KEY: K
<222> LOCATION: (24)..(24)
<223> OTHER INFORMATION: G or T
<220> FEATURE:
<221> NAME/KEY: M
<222> LOCATION: (25)..(25)
<223> OTHER INFORMATION: A or C
<220> FEATURE:
<221> NAME/KEY: H

```
<222> LOCATION: (26)..(26)
<223> OTHER INFORMATION: A, C, or T

<400> SEQUENCE: 21
rwvgbvghcm srarammrat aaakmhtaaa                                      30

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
cgaggctctc gggacgac                                                   18

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
gtcgtcccgc ctttaggatt tacag                                           25

<210> SEQ ID NO 24
<211> LENGTH: 19
<212> TYPE: DNA
<213> ORGANISM: Artificial Sequence
<220> FEATURE:
<223> OTHER INFORMATION: reporter
<220> FEATURE:
<221> NAME/KEY: k
<222> LOCATION: (19)..(19)
<223> OTHER INFORMATION: 3Cy5Sp

<400> SEQUENCE: 24
gtcgtcccga gagcctcgk                                                  19
```

LIPOTEICHOIC ACID (LTA) APTAMERS AND ASSOCIATED METHODS

CROSS-REFERENCE TO RELATED APPLICATION

This application claims the benefit under 35 U.S.C. § 119(e) of U.S. Provisional Patent Application Ser. No. 63/145,632, filed Feb. 4, 2021, the disclosure of which is hereby incorporated herein in its entirety by this reference.

TECHNICAL FIELD

This application relates generally to biochemistry, and more particularly to aptamers that specifically bind to lipoteichoic acid ("LTA") and associated methods.

STATEMENT ACCORDING TO 37 C.F.R. § 1.821(C) OR (E)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Teichoic acids are bacterial copolymers of glycerol phosphate or ribitol phosphate and carbohydrates linked via phosphodiester bonds. Teichoic acids are found within the cell wall of most Gram-positive bacteria including *Staphylococcus*, and appear to extend to the surface of the peptidoglycan layer. Teichoic acids can be covalently linked to N-acetylmuramic acid or a terminal D-alanine in the tetrapeptide cross-linkage between N-acetylmuramic acid units of the peptidoglycan layer, or they can be anchored in the cytoplasmic membrane with a lipid anchor. Teichoic acids that are anchored to the lipid membrane are referred to as "lipoteichoic acids" (or LTAs).

In Tadler et al., "Sandwich immunoassay for the detection of lipoteichoic acid," *Journal of Clinical Laboratory Analysis*. 3(1): 21-25 (1989), a sandwich immunoassay is described for detecting lipoteichoic acid. Monoclonal antibodies were produced to purified LTA from *Streptococcus mutans* (strain BHT) and were further characterized for cross-reactivity with Gram-positive and negative bacteria and for reactivity to substituted and unsubstituted LTA. Eight monoclonal antibodies were identified that reacted exclusively with Gram-positive bacteria. Antibodies that were able to capture H-LTA were chosen to develop a sandwich immunoassay, which was described as having a sensitivity of 0.2 ng LTA/mL in PBS, 0.5 ng/mL in whole blood, and 2.0 ng/mL in processed whole blood. A goal was to develop this assay for the rapid detection of LTA from body fluids.

Aptamers are short strands of oligonucleotides that form a three-dimensional structure able to bind a target material with high affinity and specificity. Aptamers can, for example, be used as elements of biosensors that can recognize molecules in detection and analysis systems, similar to antibodies.

Oligonucleotide-based aptamers have several advantages over protein-based antibodies. First, the aptamer can be synthesized in vitro, second, various organic and inorganic materials including toxins can be used as aptamer targets, and third, aptamers are more stable at various temperatures than protein antibodies.

Once aptamers have been identified and obtained, they can be reproduced with relatively low cost and high batch-consistency by automated oligomer synthesis. Further, aptamers can relatively easily be modified to introduce useful functional groups, such as fluorescent molecules or photoreactive groups.

PCT International Application PCT/KR2011/009631 (corresponding to WO 2012081908), published Jun. 21, 2012, the contents of which are incorporated herein by this reference, describes an RNA aptamer for "teichoic" acid in *Staphylococcus aureus*, and more particularly, to an RNA aptamer that specifically binds the acid in *S. aureus*, which is useful for detecting the acid in *S. aureus*, a cause of, for example, food poisoning.

RNA aptamers are somewhat less stable than their DNA counterparts. Also, RNA aptamers are less tolerant of variations in solution chemistry (pH, salts, etc.) than DNA aptamers and are more prone to lose binding affinity as the RNA aptamer's tertiary structure is affected by these variations.

SUMMARY OF THE DISCLOSURE

Described herein are DNA aptamers to LTA.

In certain embodiments, such an aptamer has a loop structure. In certain embodiments, such an aptamer has a double-stranded stem structure. In certain embodiments, such an aptamer further comprises at least one labeling substance such as an optical label, an electrochemical label, a radioisotope, or a combination thereof.

Specifically described are the exemplary DNA aptamers of SEQ ID NOs: 1-11.

(5'->3') (SEQ ID NO: 1):
CGA GGC TCT CGG GAC GAC CTG TCG TCA GGA AAA ACG

AAA ACC CTA AGG GTC GTC CCG CCT TTA GGA TTT ACA G;

(5'->3') (SEQ ID NO: 2):
CGA GGC TCT CGG GAC GAC CAG TCG GCC CGA AAA CAA

TAT AAA TCC GAG GTC GTC CCG CCT TTA GGA TTT ACA G;

(5'->3') (SEQ ID NO: 3):
CGA GGC TCT CGG GAC GAC GTA GTC GTC ACA CAA GCT

GGT TAT CCA AAA GTC GTC CCG CCT TTA GGA TTT ACA G;

(5'->3') (SEQ ID NO: 4):
CGA GGC TCT CGG GAC GAC GAA GTC GCC ACG TAA ACC

GAC GAC CGT CAG GTC GTC CCG CCT TTA GGA TTT ACA G;

(5'->3') (SEQ ID NO: 5):
CGA GGC TCT CGG GAC GAC GTG GCG GCC CGA AAA CAG

ATA AAT CAT AAA GTC GTC CCG CCT TTA GGA TTT ACA G;

(5'->3') (SEQ ID NO: 6):
CGA GGC TCT CGG GAC GAC AAA GGA GTC ACG AAA ACA

ATA AAG ACT AAA GTC GTC CCG CCT TTA GGA TTT ACA G;

(5'->3'): (SEQ ID NO 7):
CGA GGC TCT CGG GAC GAC GTC GTC GAC CCA AGA ACA

ATA AAG CTT AAA GTC GTC CCG CCT TTA GGA TTT ACA G;

-continued

```
(5'->3') (SEQ ID NO: 8):
CGA GGC TCT CGG GAC GAC GAG ACA CGC TAG TAT CGA

AGC GGC CCA AAA GTC GTC CCG CCT TTA GGA TTT ACA G;

(5'->3') (SEQ ID NO: 9):
CGA GGC TCT CGG GAC GAC TTG TCG GAC CGA CTG GTG

ATA AAC CCT ATG GTC GTC CCG CCT TTA GGA TTT ACA G;
and (5'->3') (SEQ ID NO: 10):
CGA GGC TCT CGG GAC GAC AAT ACC CGA AGG GCA TTG

CCG CCT CCA AAA GTC GTC CCG CCT TTA GGA TTT ACA G.
```

As can be seen, the "core sequences" of these aptamers are, respectively, SEQ ID NOs: 11-20:

```
(SEQ ID NO: 11):
CTG TCG TCA GGA AAA ACG AAA ACC CTA AGG;

(SEQ ID NO: 12):
CAG TCG GCC CGA AAA CAA TAT AAA TCC GAG;

(SEQ ID NO: 13):
GTA GTC GTC ACA CAA GCT GGT TAT CCA AAA;

(SEQ ID NO: 14):
GAA GTC GCC ACG TAA ACC GAC GAC CGT CAG;

(SEQ ID NO: 15):
GTG GCG GCC CGA AAA CAG ATA AAT CAT AAA;

(SEQ ID NO: 16):
AAA GGA GTC ACG AAA ACA ATA AAG ACT AAA;

(SEQ ID NO: 17):
GTC GTC GAC CCA AGA ACA ATA AAG CTT AAA;

(SEQ ID NO: 18):
GAG ACA CGC TAG TAT CGA AGC GGC CCA AAA;

(SEQ ID NO: 19):
TTG TCG GAC CGA CTG GTG ATA AAC CCT ATG;
and (SEQ ID NO: 20):
AAT ACC CGA AGG GCA TTG CCG CCT CCA AAA.
```

In certain embodiments, the DNA aptamer core sequence is (SEQ ID NO: 21):
RWV GBV GHC MSR ARA MMR ATA AAK MHT AAA-
wherein A, C, G, and T have their customary meaning, wherein R is A or G; wherein W is A or T; wherein V is A, C, or G; wherein B is C, G, or T; wherein H is A, C, or T; wherein M is A or C; wherein S is C or G; wherein K is G or T.

The aptamers of SEQ ID NOs: 1-10 also include PCR primer annealing regions (or "primer sequences") (5'-CGA GGC TCT CGG GAC GAC (SEQ ID NO:22)-[core sequence]-GTC GTC CCG CCT TTA GGA TTT ACA G-3' (SEQ ID NO:23)), although other PCR primer annealing regions may be used so long as they do not interfere with the binding of the aptamer to LTA.

Thus, described is a DNA aptamer comprising a polynucleotide of any of the following (a) to (c) and capable of binding to lipoteichoic acid ("LTA"): (a) a polynucleotide comprising a core sequence set forth in any one of SEQ ID NOs: 11-21, (b) a polynucleotide comprising a core sequence having the deletion, substitution, insertion and/or addition of one to two bases in the core sequence set forth in any one of SEQ ID NOs: 11-21, and (c) a polynucleotide comprising a core sequence having a sequence identity of 80% or more to the core sequence set forth in any one of SEQ ID NOs: 11-21.

In certain embodiments, provided is a method for detecting LTA, including binding an aptamer as described herein to LTA to thereby detect the LTA.

Thus, further described herein are the DNA aptamers and their use for detecting LTA.

DETAILED DESCRIPTION

Figure 1A:
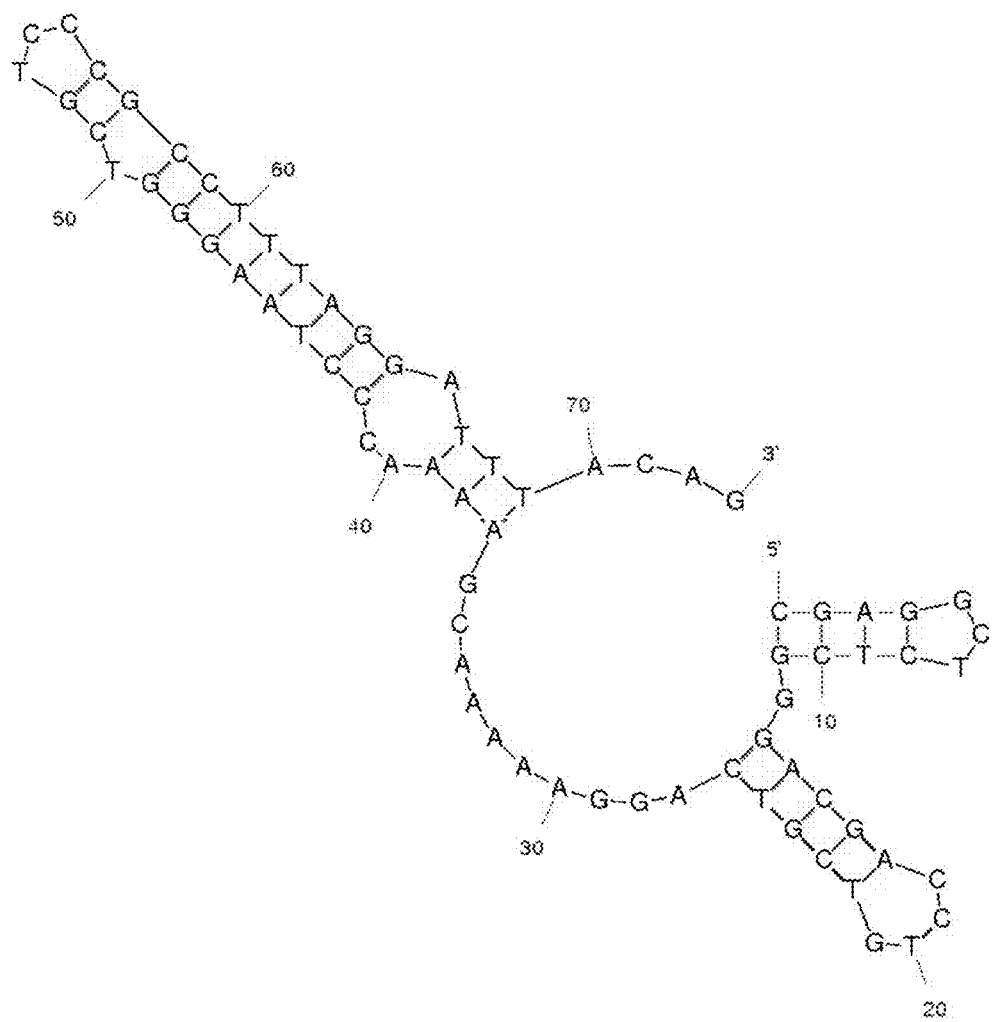
FIGS. 1A-1E show the predicted secondary structures of the DNA aptamers of SEQ ID NOs: 1-5.

The term "base pairing," as used herein, refers to base pairing formed of a pair of complementary synthetic bases, such as adenine and thymine or guanine and cytosine.

The term "DNA aptamer," as used herein, refers to an aptamer sequence composed of DNA molecules. A DNA aptamer is a ligand molecule that firmly and specifically binds to a target molecule through a conformational structure formed based upon a secondary and a tertiary structure of a single-stranded nucleic acid molecule via hydrogen bonding or other interactions.

The term "target molecule," as used herein, refers to a substance to which the DNA aptamer can bind. For instance, a target molecule is LTA.

In one aspect, described is an agent for detecting LTA, the agent comprising the DNA aptamer as described herein. In certain embodiments, the agent for detecting LTA is an agent that is used for detecting LTA in vitro utilizing the ability of a described DNA aptamer to bind to LTA. For example, the DNA aptamer is labeled with a fluorescence reagent beforehand, and the labeled DNA aptamer is admixed with a sample.

In one aspect, described is a composition for detecting LTA, the composition comprising a DNA aptamer as described herein.

In principle, the composition may be prepared in accordance with a method known in the art. For example, see the method described in Remington's Pharmaceutical Sciences (Merck Publishing Co., Easton, Pa.).

For example, preparations can be prepared by a method generally used in the art, comprising dissolving at least one DNA aptamer hereof in, for example, a pharmaceutically acceptable solvent and adding, for example, a pharmaceutically acceptable carrier thereto, if needed.

Examples of "pharmaceutically acceptable solvent(s)" include water, ethanol, propylene glycol, ethoxylated isostearyl alcohol, polyoxylated isostearyl alcohol, and a polyoxyethylene sorbitan fatty acid ester.

In one aspect, the disclosure relates to a kit for detecting LTA or for more generally detecting gram-positive bacteria is a sample, the kit comprising the DNA aptamer as described herein. In addition to the DNA aptamer as described herein, the kit as described herein may comprise, for example, a buffer, a label reagent, and/or instructions.

In certain embodiments, the aptamer is labeled with a labeling substance, and detection of the LTA may occur by detecting the labeling substance. Examples of labeling substances include a dye, a fluorescent dye, a radioisotope, an antibody, an antigen, and an enzyme. Examples of the fluorescent dye include FITC. Such labels may be attached to a specific base or a specific structure of the aptamer, for example, a specific site of a hairpin-loop structure or a 3' or 5' terminus of an aptamer.

An optical label may be exemplified by a fluorescent material. For example, the fluorescent material may be selected from among fluorescein, 6-FAM, rhodamine, Texas Red, tetramethyl rhodamine, carboxyl rhodamine, carboxyl rhodamine 6G, carboxyl rhodol, carboxyl rhodamine 110, Cascade Blue, Cascade Yellow, coumarin, Cy2 (cyanine 2), Cy3, Cy3.5, Cy5, Cy5.5, Cy-chromium, phycoerythrin, PerCP (peridinin chlorophyll—a protein), PerCP-Cy5.5, JOE (6-carboxy-4',5'-dichloro-2',7'-dimethoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, conjugations thereof, and combinations thereof.

The optical label may be an enzyme, suitable for use in enzyme-linked immunosorbent assay ("ELISA"). The enzyme used for ELISA may include alkaline phosphatase, horseradish peroxidase, luciferase, or glucose oxidase. When the enzyme is used as the optical label, a chemiluminescent material may be employed in order to induce a chemiluminescent reaction, the chemiluminescent material being selected from among luminol, isoluminol, luciferin, lucigenin, 3-(2'-spiroadamantane)-4-methoxy-4-(3''-phosphoryloxy)phenyl-1,2-dioxetan-e (AMPPD), and disodium 3-(4-methoxyspiro {1,2-dioxetane-3,2'-(5'-chloro)tricyclo [3.3.1.13,7]decan}-4-yl)phenyl phosphate (CSPD). In addition thereto, any material appropriately selected by those skilled in the art is useful.

An optical label may be a fluorescence resonance energy transfer ("FRET") pair, which includes a donor fluorophore and an acceptor fluorophore spaced apart from each other by an appropriate distance and in which the fluorescence emission of the donor is suppressed or quenched by the acceptor. The donor fluorophore may include FAM, TAMRA, VIC, JOE, Cy3, Cy5 and Texas Red. The acceptor fluorophore may be selected so as to overlap its excitation spectrum with the emission spectrum of the donor. The acceptor may be a non-fluorescence acceptor for quenching a wide range of donor.

Also described herein is an aptamer-immobilized carrier in which the aptamer for detecting LTA (or a multi-structure aptamer thereof) is immobilized on the surface of a solid phase carrier. As the solid phase carrier, it is possible to employ carriers of various shapes such as sheet-like, plate-like, cylindrical, and spherical carriers. As the material for a carrier, a plastic, metal, glass, or the like may be used. Typically, any material may be used so long as it is a material able to have an aptamer immobilized thereto, for example for use with a lateral flow assay device. (See, e.g., United States Patent Application 20200249228 A1 to Jiang et al. (Aug. 6, 2020) for "Rapid Diagnosis of Peritonitis in Peritoneal Dialysis Patients," the contents of which are incorporated herein by this reference.) For example, an aptamer-immobilized carrier may be a carrier in which the aptamer is immobilized on the surface of a sheet-like solid phase carrier.

The invention is further described with the aid of the following illustrative Examples.

EXAMPLES

Example I

After screening a nucleic acid library over several generations against the target lipoteichoic acid (LTA) for specificity over counter-targets, for example, lipopolysaccharides (LPS), peptidoglycans, the enriched library was processed to identify aptamer candidates. Libraries produced by initial screening were sequenced for used in the differential analysis and identification of the most promising aptamer sequences in terms of binding performance. These candidates were qualitatively assessed for response to LTA in 1×SELEX buffer before the best candidates were characterized.

As will be appreciated by those of skill in the art, SELEX begins with the synthesis of a very large oligonucleotide library consisting of randomly generated sequences of fixed length flanked by constant 5' and 3' ends that serve as primers. For a randomly generated region of length n, the number of possible sequences in the library is 4n (n positions with four possibilities (A, T, C, or G) at each position). The sequences in the library are exposed to the target ligand—which may be a protein or a small organic compound—and those that do not bind the target are removed, usually by affinity chromatography or target capture on paramagnetic beads. The bound sequences are eluted and amplified by PCR to prepare for subsequent rounds of selection in which the stringency of the elution conditions can be increased to identify the tightest-binding sequences.

Sequencing: The initial library was subjected to nine rounds of Melting-Off selection followed by parallel assessment. The SELEX process enriches for sequences over multiple rounds of selection that bind to LTA, and remove sequences that respond to components of 1×SELEX buffer or LPS. As a result, the population to be sequenced should contain multiple copies of potential aptamer candidates.

An Illumina (San Diego, CA, US) MiniSeq™ system was used to sequence the aptamer libraries after the post-parallel selection using a single-end read technique. Deep sequencing and subsequent data analysis simplifies the traditional approach of performing a large number of screening rounds (Schütze et al., 2011). Numerous sequences were analyzed from the parallel-exposed final libraries. From these sets of data, the library sequence families were constructed at 90% homology (sequence similarity considering mutations, deletions, and insertions).

Bioinformatics and Aptamer Candidate Selection: An individual sequence's frequency in the positive target population was factored in, but the degree of variation between similar sequences was also important, with 90% homology being the minimum requirement (100% match over the entire sequence is not necessary to join a family; up to 2 bases can be mismatched, inserted, or deleted).

One factor is the presence of a sequence in the non-positive-target-exposed populations. Four libraries were collected for sequencing: the post-parallel assessment library that had been recovered from incubation with a positive target in 1×SELEX buffer; post-parallel assessment library recovered after incubation with LPS in 1×SELEX buffer; post-parallel assessment library recovered after incubation with 1×SELEX buffer only; and the parallel assessment library recovered from incubation with LTA in 1×SELEX buffer. The positive population was compared against the counter population to identify sequences that were not removed during the counter selection steps, but which still had affinity for both LTA and LPS. A candidate's rate of enrichment was also considered (see, e.g., Wang et al., 2014). 200 candidates were chosen for microarray synthesis and high throughput assessment.

Figure 1B:
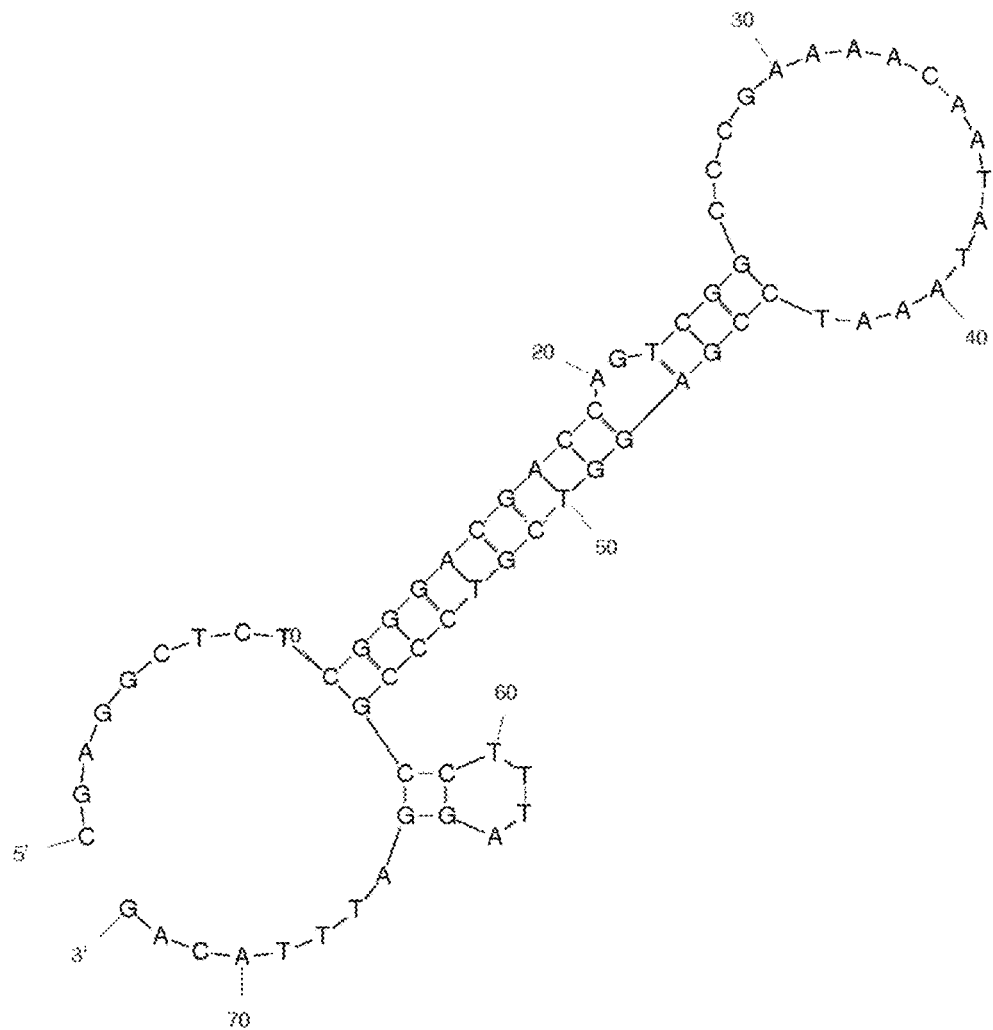
Figure 1C:
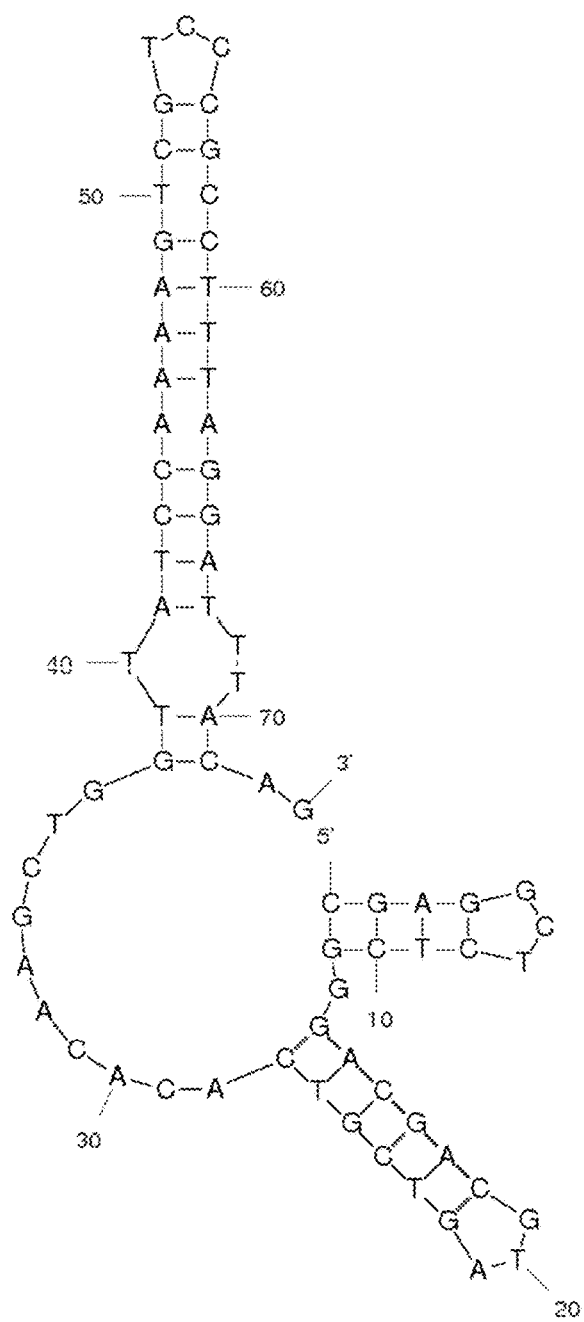
Figure 1D:
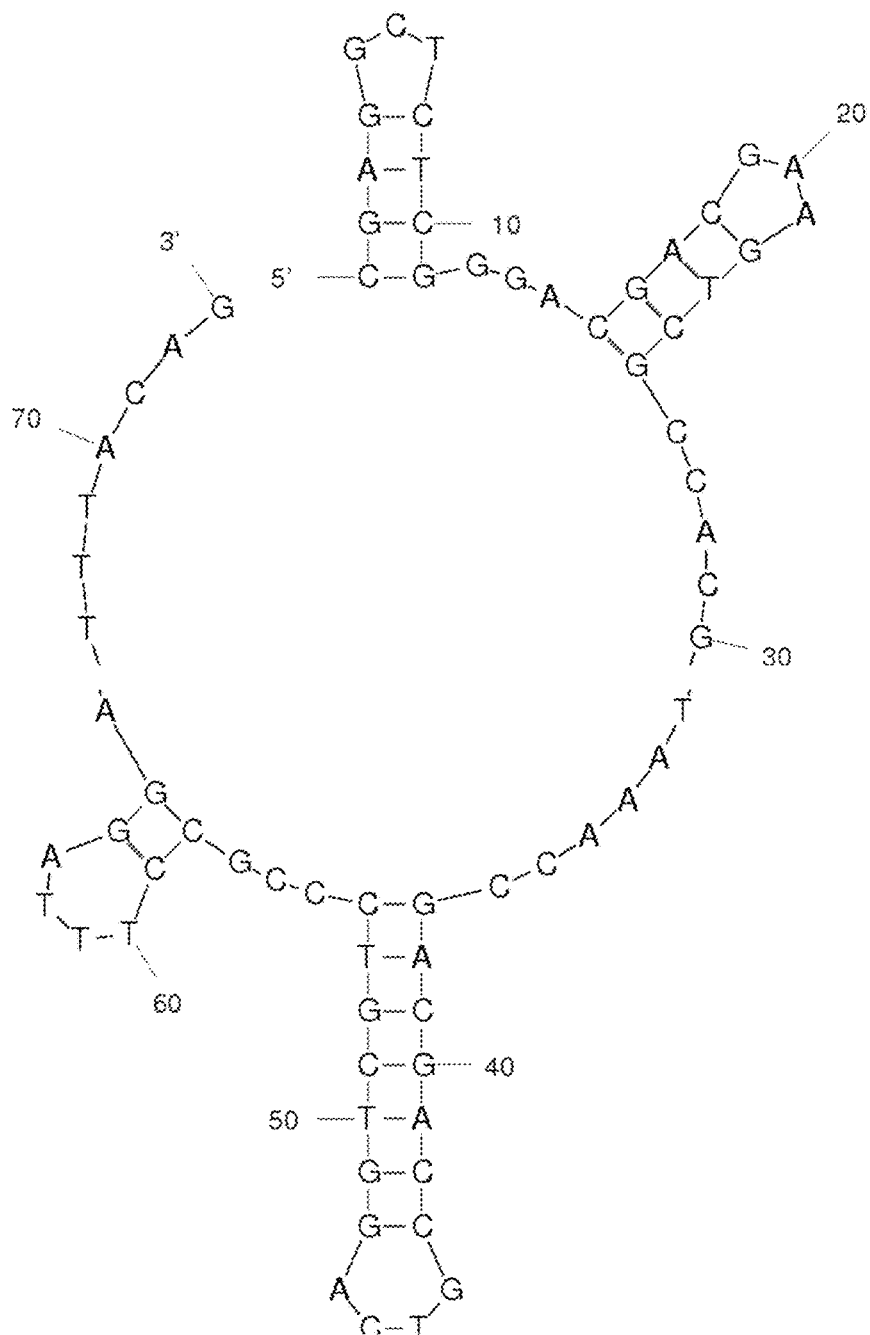
Figure 1E:
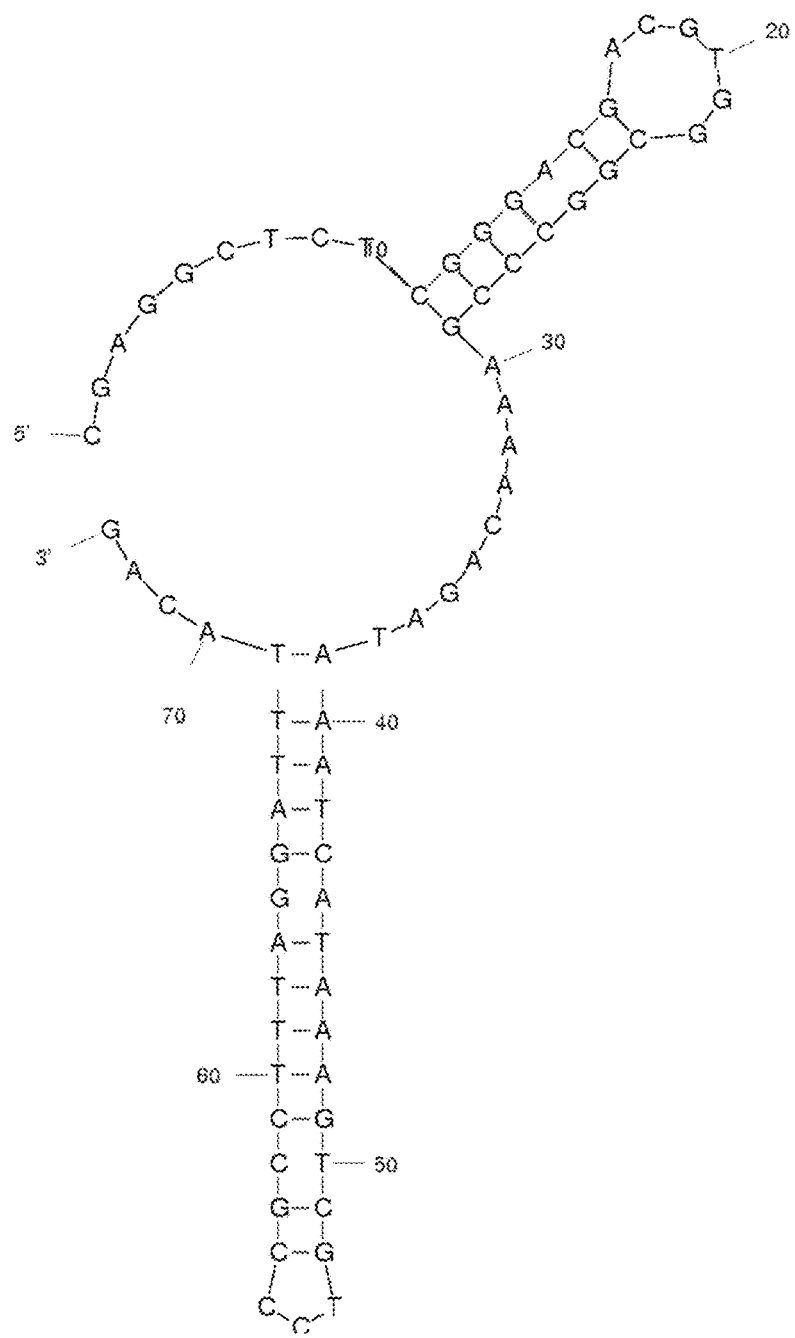
Figure 2A:
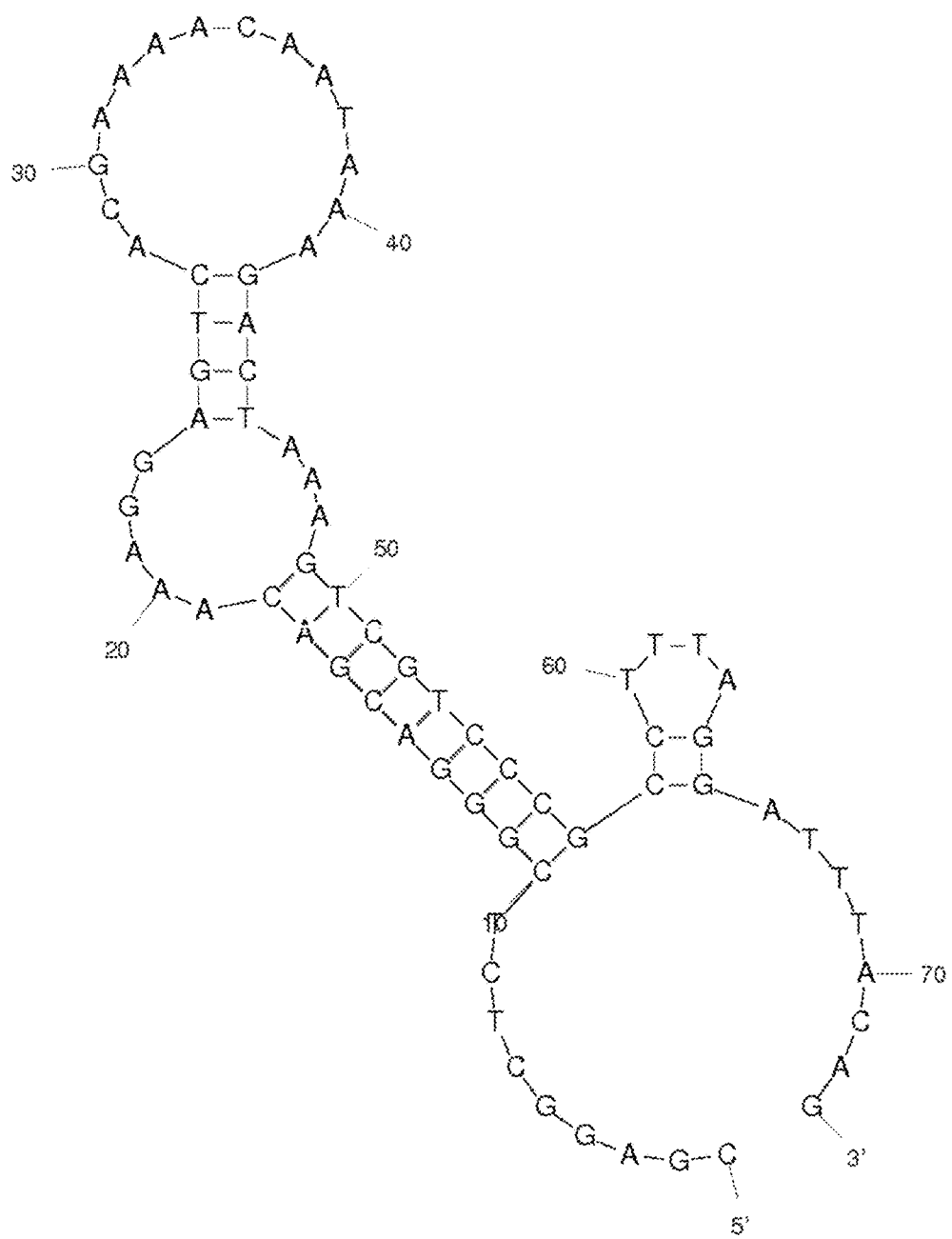
FIGS. 2A-2E show the predicted secondary structures of the DNA aptamers of SEQ ID NOs: 6-10.
Figure 2B:
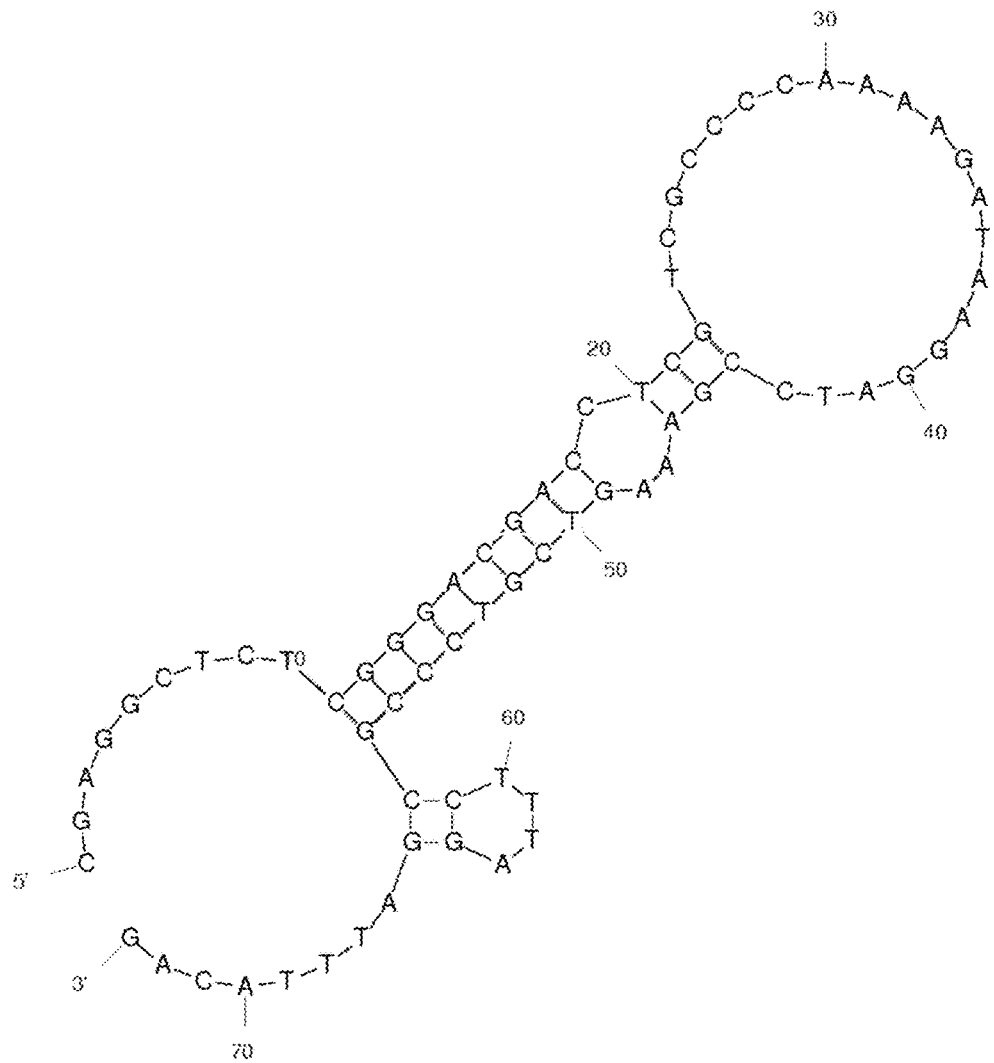
Figure 2C:
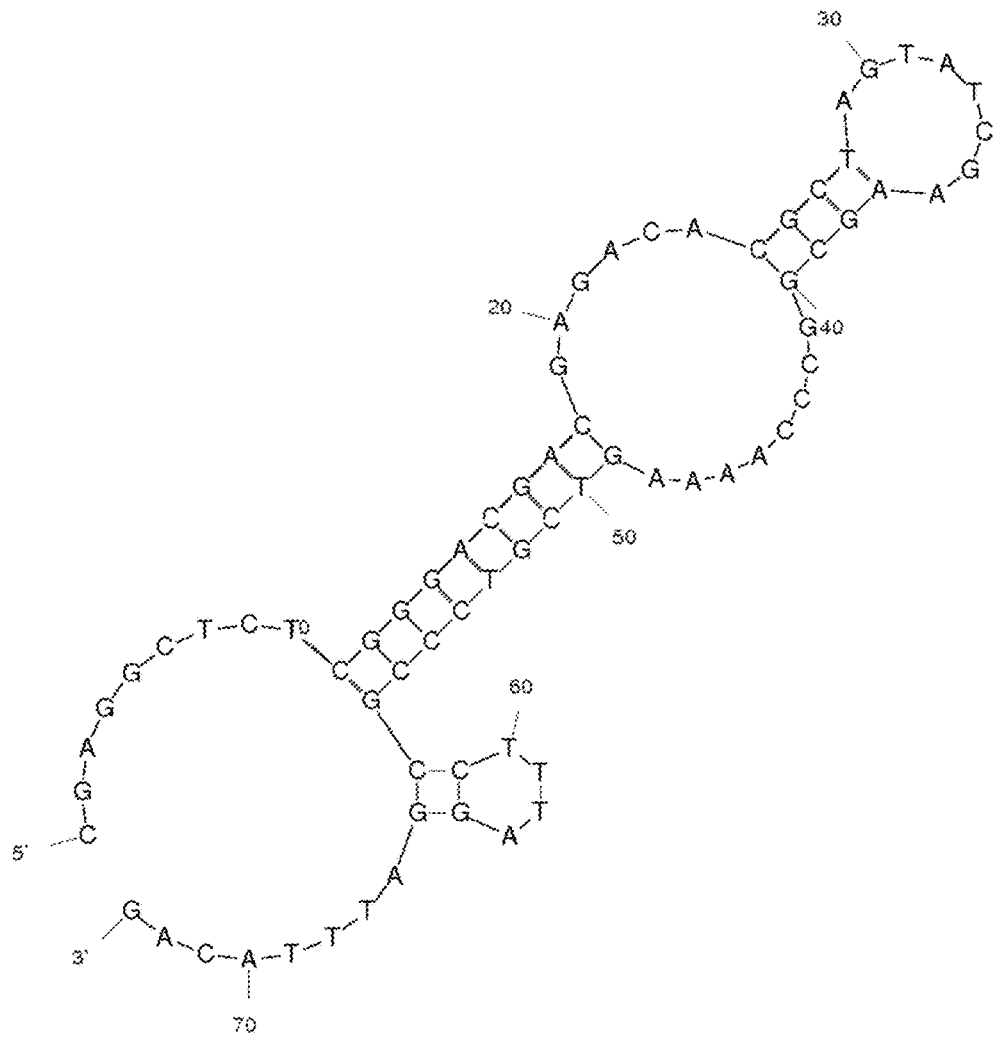
Figure 2D:
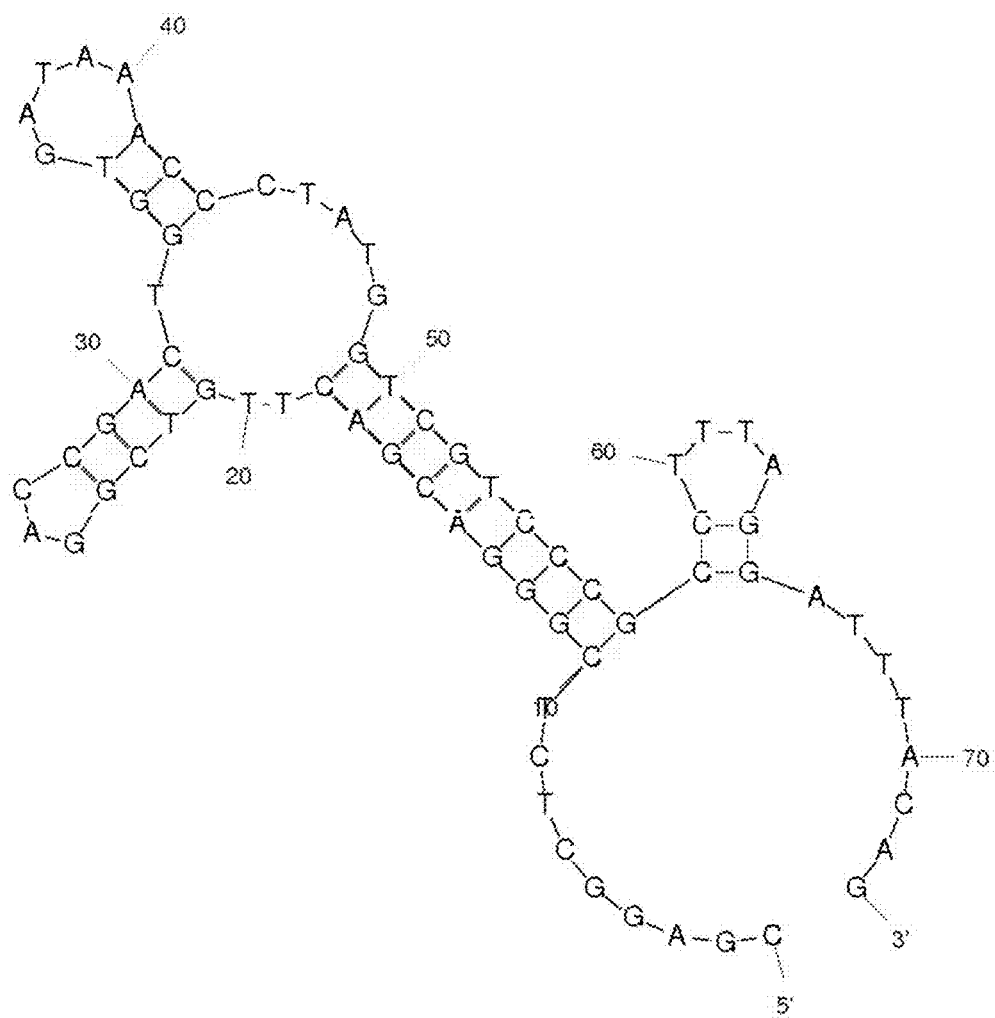
Figure 2E:
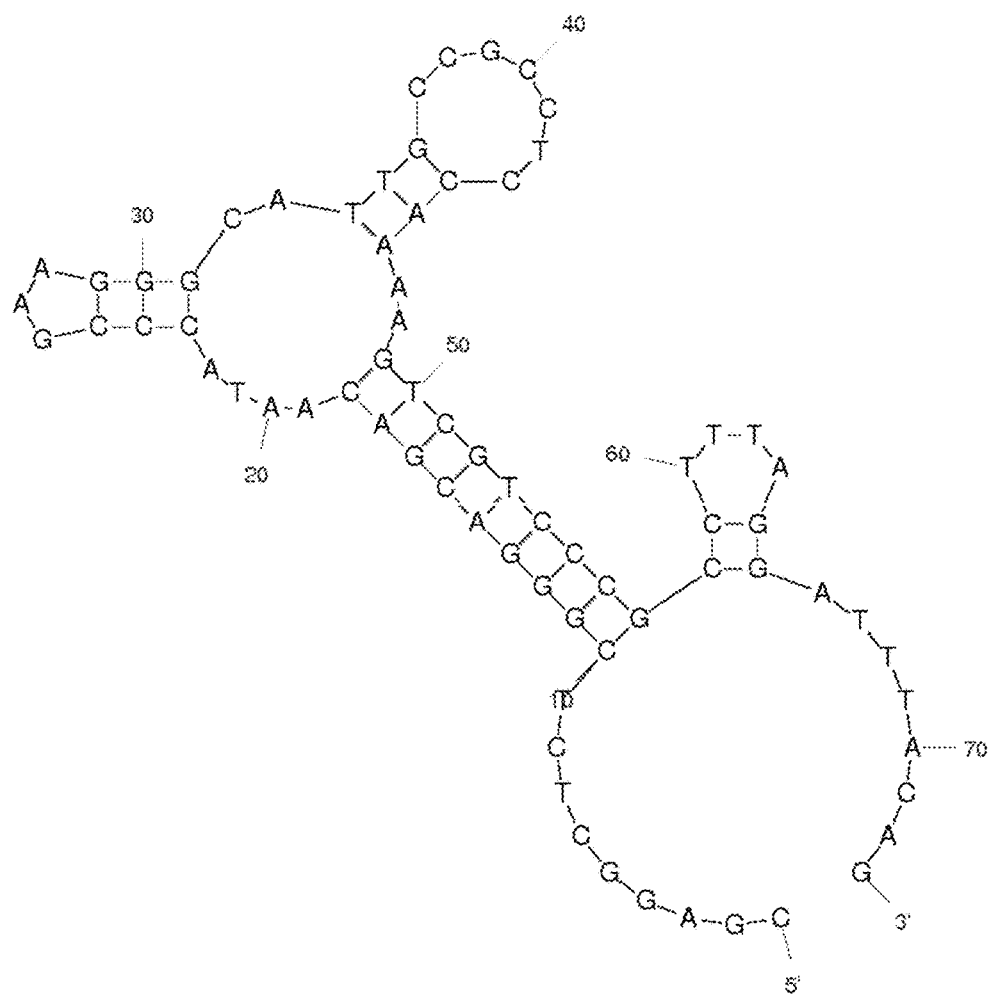

From these 200 aptamer candidates, SEQ ID NOs:1-5 were specifically identified as examples of the selection process (FIGS. 1A-1E). The most prevalent family in the population is also highly present in the counter population. However, this sequence (and similar sequences) appeared at high enough frequencies in the positive populations to be still worth investigating in a high-throughput analysis. SEQ ID NOs: 1-5 were selected on the basis of greater proportional representation in the positive population over the counter population and/or negative population.

Finally, all candidate sequences exhibited sufficient stability based upon mfold secondary structure prediction to be considered candidates (FIGS. 1A-1E).

Microarray Synthesis and Semi-Quantitative Assessment

Microarray Methods: A Cy5-labeled reporter oligonucleotide complimentary to a constant region of the library (5'-GTC GTC CCG AGA GCC TCG/3Cy5Sp/-3' (SEQ ID NO:24)) was synthesized. SEQ ID NO:24 would be displaced during target binding. Oligonucleotides underwent desalting purification.

Data analysis was conducted as follows. The mean background fluorescence value was subtracted from the mean fluorescence value of each candidate prior to the addition of sample as well as each candidate after the addition of sample.

Microarray Results: Candidates were first tested against 100 ng/mL target LTA sample. The result of blocking candidates with Reporter oligonucleotide was imaged. Based upon the image, most candidates interacted well with the Reporter. After this reading was taken, candidates were incubated with target sample overnight at 23° C. The solution at the inlet of the peristaltic pump was then replaced with 1×SELEX buffer to displace the target sample in the microarray.

The same processes were used to analyze candidate response to 1 µg/mL of counter target LPS sample, of which the second run data is presented.

Candidate percent responses to target sample and counter target sample were calculated as the mean of 18 replicate positions. The percent responses themselves were compared to determine candidates that specifically responded to the target. Candidates were ranked according to the ratio of signal loss to the target condition against the signal loss to the counter condition. The greater this score, the more response to the target condition relative to the response to the counter condition. The aptamer candidates with the top five scores (SEQ ID NOs. 6-10) were then synthesized for qualitative assessment.

Monoclonal Synthesis and Qualitative Validation:

Assessment Methods: SEQ ID NOs.: 6-10 were synthesized and purified by desalting. Assessment followed a method similar to that used in the previously described SELEX.

Assessment Results: Initial assessment was carried out with SEQ ID NOs.: 6-10 against just target LTA in 1×SELEX Buffer to determine which candidates demonstrated noticeable response. Differences in the intensity of material present in the candidate lanes represented different amounts of candidate released from magnetic beads as a result of incubation with, and binding to, target LTA. Based upon these results, candidates SEQ ID NO:6, SEQ ID NO:8, and SEQ ID NO:9 were selected for additional assessment against counter-target LPS.

The chosen candidates were re-assessed against both target and counter-target in the presence of patient samples. Candidate SEQ ID NO:6 ran in a pattern similar to other samples that were known to have had a high concentration of sugar. SEQ ID NO:9 showed stronger response to target over counter-target.

Example II

An aptamer comprising a core sequence selected from the group consisting of SEQ ID NOs: 11-21 is appropriately labeled with quenching labels and used in an assay to detect LTA in a medical sample taken from a patient (e.g., peritoneal dialysis fluid). The assay is thus used to detect the presence of gram-positive bacteria in the medical sample so as to diagnose an infection in the subject for treatment with an appropriate antibiotic.

REFERENCES (the contents of the entirety of each of which is incorporated herein by this reference):

Ellington and Szostak, "In vitro selection of RNA molecules that bind specific Ligands," Nature 1990, 346, 818.

Gold et al., "Aptamers and the RNA world, past and present," Cold Spring Harb. Perspect. Biol. 2012, 4, a003582.

Schütze et al., "Probing the SELEX Process with Next-Generation Sequencing," PLoS ONE 6(12): e29604 (2011). DOI: 10.1371/journal.pone.0029604.

Tuerk et al., "Systematic evolution of ligands by exponential enrichment: RNA ligands to bacteriophage t4 DNA polymerase," Science 1990, 249, 505-510.

Wang et al., "Particle Display: A Quantitative Screening Method for Generating High-Affinity Aptamers," Angewandte Communications International Edition 53: 4796-4801 (2014). DOI: 10.1002/anie.201309334.

Zhuo et al., "Recent Advances in SELEX Technology and Aptamer Applications in Biomedicine," Int. J. Mol. Sci. 2017, 18, 2142; doi:10.3390/ijms18102142.

M. Zuker, "Mfold web server for nucleic acid folding and hybridization prediction," Nucleic Acids Res. 31(13): 3406-3415 (2003). mfold.rna.albany.edu/?q=DINAMelt/Quickfold.

US Patent Application Publication 20200249228 A1 to Jiang et al. (Aug. 6, 2020) for "Rapid Diagnosis of Peritonitis in Peritoneal Dialysis Patients."

What is claimed is:

1. A DNA aptamer comprising a polynucleotide capable of binding to lipoteichoic acid ("LTA"), wherein the polynucleotide comprises:
   (a) a polynucleotide comprising a core sequence set forth in any one of SEQ ID NOs: 11-20, or
   (b) a polynucleotide comprising a sequence set forth in any one of SEQ ID NOs: 1-10.

2. The DNA aptamer of claim 1, wherein the DNA aptamer has a loop structure.

3. The DNA aptamer of claim 1, wherein the DNA aptamer has a double-stranded stem structure.

4. The DNA aptamer of claim 1, further comprising at least one labeling sub stance.

5. The DNA aptamer of claim 4, wherein the at least one labeling substance is an optical label, an electrochemical label, a radioisotope, or a combination thereof.

6. The DNA aptamer of claim 1, wherein the DNA aptamer has the core sequence of SEQ ID NO: 11.

7. The DNA aptamer of claim 1, wherein the DNA aptamer has the core sequence of SEQ ID NO: 12.

8. The DNA aptamer of claim 1, wherein the DNA aptamer has the core sequence of SEQ ID NO: 13.

9. The DNA aptamer of claim 1, wherein the DNA aptamer has the core sequence of SEQ ID NO: 14.

10. The DNA aptamer of claim 1, wherein the DNA aptamer has the core sequence of SEQ ID NO: 15.

11. A DNA aptamer comprising a polynucleotide capable of binding to lipoteichoic acid ("LTA"), wherein the DNA aptamer comprises a core sequence set forth in any one of SEQ ID NOs: 16-20.

12. The DNA aptamer of claim 11, wherein the DNA aptamer has the core sequence of SEQ ID NO: 17.

13. The DNA aptamer of claim 11, wherein the DNA aptamer has the core sequence of SEQ ID NO: 18.

14. The DNA aptamer of claim 11, wherein the DNA aptamer has the core sequence of SEQ ID NO: 19.

15. The DNA aptamer of claim 11, wherein the DNA aptamer has the core sequence of SEQ ID NO: 20.

16. The DNA aptamer of claim 1, further comprising:
   SEQ ID NO:22 and/or SEQ ID NO:23.

17. A biosensor for detecting *Staphylococcus*, the biosensor comprising:
   the DNA aptamer of claim 1, and
   a substrate to which the DNA aptamer is fixed.

18. The biosensor of claim 17, further comprising:
   a linker between the substrate and the DNA aptamer.

19. A method of detecting lipoteichoic acid ("LTA") in a sample, the method comprising:
   utilizing the DNA aptamer of claim 1 to detect the LTA in the sample.

20. The DNA aptamer of claim 11, wherein the DNA aptamer has the core sequence of SEQ ID NO: 16.

* * * * *